United States Patent
Ahn et al.

(10) Patent No.: US 9,322,902 B2
(45) Date of Patent: Apr. 26, 2016

(54) ULTRASOUND SYSTEM AND METHOD FOR FORMING COMBINED BC-MODE IMAGE

(75) Inventors: Chi Young Ahn, Seoul (KR); Woo Youl Lee, Seoul (KR)

(73) Assignee: SAMSUNG MEDISON CO., LTD., Hongcheon-gun, Gangwon-do (KR)

( * ) Notice: Subject to any disclaimer, the term of this patent is extended or adjusted under 35 U.S.C. 154(b) by 148 days.

(21) Appl. No.: 13/438,553

(22) Filed: Apr. 3, 2012

(65) Prior Publication Data
US 2012/0265073 A1   Oct. 18, 2012

Related U.S. Application Data

(63) Continuation of application No. 12/270,750, filed on Nov. 13, 2008, now Pat. No. 8,216,141.

(30) Foreign Application Priority Data

Nov. 14, 2007   (KR) .................. 10-2007-0116212

(51) Int. Cl.
*A61B 8/14* (2006.01)
*G01S 7/52* (2006.01)
*G01S 15/89* (2006.01)
*A61B 8/08* (2006.01)

(52) U.S. Cl.
CPC .......... *G01S 7/52025* (2013.01); *G01S 7/52063* (2013.01); *G01S 7/52085* (2013.01); *G01S 15/8988* (2013.01); *A61B 8/08* (2013.01)

(58) Field of Classification Search
None
See application file for complete search history.

(56) References Cited

U.S. PATENT DOCUMENTS

| | | | |
|---|---|---|---|
| 4,228,804 A | 10/1980 | Holasek et al. | |
| 5,301,670 A | 4/1994 | Sato et al. | |
| 5,492,125 A | 2/1996 | Kim et al. | |
| 5,509,413 A | 4/1996 | Akama et al. | |
| 5,882,315 A | 3/1999 | Ji et al. | |
| 5,931,784 A | 8/1999 | Kajiwara et al. | |

(Continued)

FOREIGN PATENT DOCUMENTS

| | | |
|---|---|---|
| JP | 04-317639 | 11/1992 |
| JP | 06-178777 A | 6/1994 |

(Continued)

OTHER PUBLICATIONS

Korean Notice of Allowance, issued in Korean Patent Application No. KR 10-2007-0116212 dated Jul. 1, 2011.

(Continued)

*Primary Examiner* — James Kish
*Assistant Examiner* — Serkan Akar
(74) *Attorney, Agent, or Firm* — McDermott Will & Emery LLP

(57) ABSTRACT

A BC-mode image with an improved frame rate in an ultrasound system is formed. A transmit/receive unit forms first and second receive signals responsive to first and second control signals. An image processing unit is configured to form a B-mode image and a C-mode image based the first and second receive signals and to combine them to form a BC-mode image. The control signal generates a third control signal for a B-mode scan along scan lines, which are not within the color box to form third receive signals. The control unit repeatedly generates the second and third control signals. The image processing unit is further operable to form a B-mode image based on the third receive signals and the second signals.

6 Claims, 7 Drawing Sheets

(56) References Cited

U.S. PATENT DOCUMENTS

| | | | |
|---|---|---|---|
| 6,071,240 | A | 6/2000 | Hall et al. |
| 6,139,501 | A | 10/2000 | Roundhill et al. |
| 6,176,830 | B1 | 1/2001 | Freiburger |
| 6,210,168 | B1 | 4/2001 | Aiger et al. |
| 6,450,961 | B1 | 9/2002 | Shiki et al. |
| 6,537,217 | B1 | 3/2003 | Bjaerum et al. |
| 6,733,449 | B1 | 5/2004 | Krishnamurthy et al. |
| 6,932,767 | B2 | 8/2005 | Landry et al. |
| 7,771,355 | B2 | 8/2010 | Lin et al. |
| 2003/0045795 | A1 | 3/2003 | Bjaerum et al. |
| 2004/0073113 | A1 | 4/2004 | Salgo et al. |
| 2004/0186379 | A1 | 9/2004 | Landry et al. |
| 2005/0093859 | A1 | 5/2005 | Sumanaweera et al. |
| 2005/0203401 | A1 | 9/2005 | Takimoto |
| 2005/0251040 | A1 | 11/2005 | Relkuntwar et al. |
| 2005/0267367 | A1 | 12/2005 | Kerby et al. |
| 2006/0079778 | A1 | 4/2006 | Mo et al. |
| 2006/0100515 | A1* | 5/2006 | Nakata .................. 600/441 |
| 2007/0038104 | A1 | 2/2007 | Hyun |
| 2007/0054645 | A1 | 3/2007 | Pan |
| 2007/0078347 | A1 | 4/2007 | Srinivasan et al. |
| 2007/0081576 | A1 | 4/2007 | Ramamurthy et al. |
| 2007/0239015 | A1 | 10/2007 | Sato |
| 2007/0241828 | A1 | 10/2007 | Nakamura et al. |

FOREIGN PATENT DOCUMENTS

| | | |
|---|---|---|
| JP | 06-269453 | 9/1994 |
| JP | 08-336534 | 12/1996 |
| JP | 2000-287972 A | 10/2000 |
| JP | 2001-037757 A | 2/2001 |
| JP | 2003-501177 A | 1/2003 |
| JP | 2003-111759 A | 4/2003 |
| JP | 2005-040225 A | 2/2005 |
| JP | 2005-058332 A | 3/2005 |
| JP | 2005-168585 A | 6/2005 |
| JP | 2006-116149 A | 5/2006 |
| JP | 2007-502685 A | 2/2007 |
| JP | 2007-222390 A | 9/2007 |
| KR | 10-1999-0014883 A | 2/1999 |
| KR | 10-2007-0000565 A | 1/2007 |
| KR | 10-2007-0024096 A | 3/2007 |
| WO | 00/75689 A1 | 12/2000 |
| WO | 2004/106969 A2 | 12/2004 |

OTHER PUBLICATIONS

Extended European Search Report issued in European Patent Application No. EP 08019747.8 dated Mar. 25, 2013.

Japanese Office Action issued in Japanese Patent Application No. JP 2008-292106 dated Apr. 16, 2013.

J. Kirkhorn et al., "A New Technique for Improved Spatial Resolution in High Frame Rate Color Doppler Imaging," 2003 IEEE Ultrasonics Symposium, 5 pages.

* cited by examiner

ULTRASOUND SYSTEM AND METHOD FOR FORMING COMBINED BC-MODE IMAGE

CROSS-REFERENCE TO RELATED APPLICATIONS

The present application is a Continuation of U.S. application Ser. No. 12/270,750 filed on Nov. 13, 2008 now U.S. Pat. No. 8,216,141, which claims priority from Korean Patent Application No. 10-2007-0116212 filed on Nov. 14, 2007, the entire subject matter of each of which is incorporated herein by reference.

BACKGROUND OF THE INVENTION

1. Technical Field

The present invention generally relates to ultrasound systems, and more particularly to an ultrasound system and a method for forming a BC-mode image.

2. Background Art

An ultrasound system has become an important and popular diagnostic tool due to its non-invasive and non-destructive nature. Modern high-performance ultrasound imaging diagnostic systems and techniques are commonly used to produce two- or three-dimensional images of internal features of patients.

The ultrasound system may provide a BC-mode image indicating a blood flow or a motion of a target object, which is estimated by using a Doppler effect, on a B-mode image. The BC-mode image is a combination image comprising a B-mode image of a grey scale and a color flow image (i.e., C-mode image) indicating the blood flow or the motion of the target object. The BC-mode image may provide anatomical information as well as information regarding the blood flow or the motion of the target object.

The conventional ultrasound image may form the B-mode image and the C-mode image with different frame rates and then combine the B-mode image with the C-mode image to thereby form the BC-mode image. Since the frame rate of the BC-mode may not be enough to obtain information regarding blood flow or the motion of the target object such as a cardiac muscle, the frame rate of the BC-mode must be improved such that motion information of the target object such as a cardiac muscle, which is rapidly moved, can be accurately provided.

DETAILED DESCRIPTION OF THE INVENTION

Figure 1:
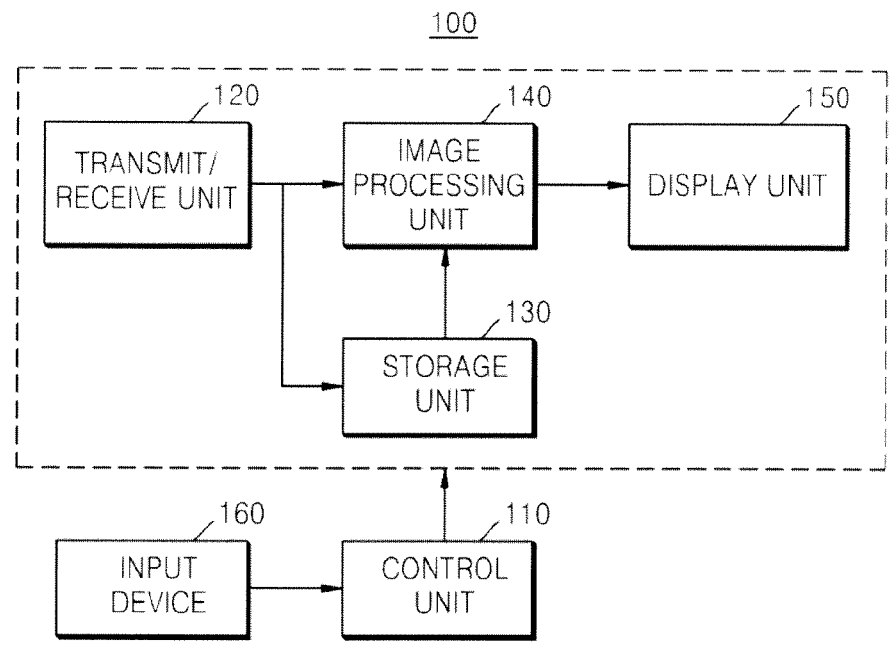
FIG. 1 is a block diagram showing an embodiment of an ultrasound system.

FIG. 1 is a block diagram showing an embodiment of an ultrasound system. As shown in FIG. 1, the ultrasound system 100 may include a control unit 110, a transmit/receive unit 120, a storage unit 130 such as a memory, an image processing unit 140 such as an image processor implemented in a computer and a display unit 150. The ultrasound system 110 may further include an input unit such as a keyboard or a mouse (not shown) to receive input information from a user. The input information may include setup information for setting a color box on a B-mode image, i.e., position and size information of the color box.

The control unit 110 may be operable to control the formation of a BC-mode image in consideration of a time required to form a B-mode image and a time required to form a C-mode image. The control unit 110 may be further operable to control operations of the transmit/receive unit 120, the storage unit 130, the image processing unit 140 and the display unit 150.

Figure 2:
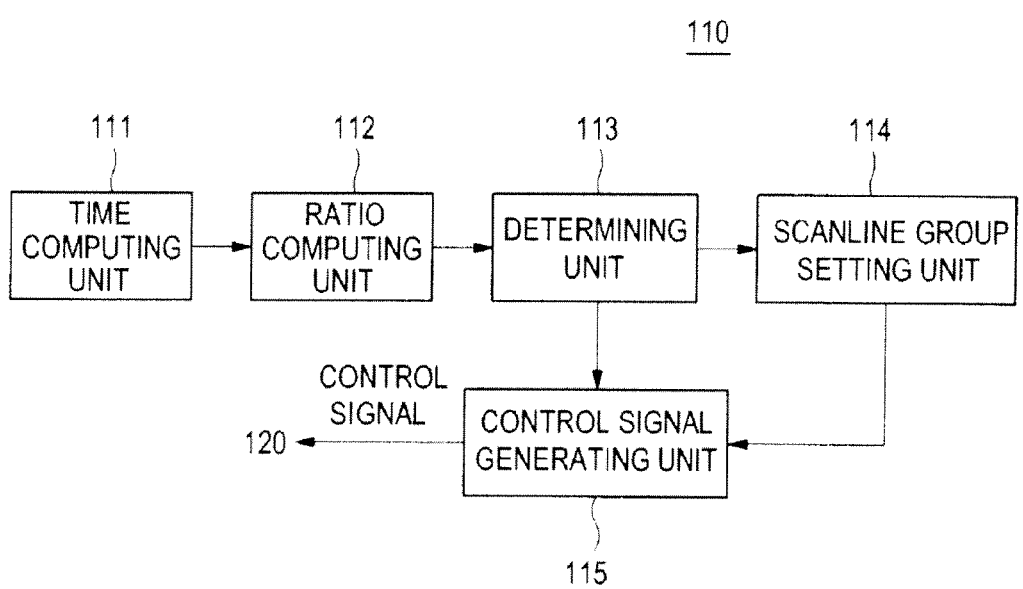
FIG. 2 is a schematic diagram showing an embodiment of a control unit.

FIG. 2 is a block diagram showing an illustrative embodiment of the control unit 110. A time computing unit 111 may be operable to compute a time required to form a B-mode image ("first time") and a time required to form a C-mode image ("second time"). The first time ($T_B$) and the second time ($T_C$) may be computed by using the following equations (1) and (2).

$$T_B = N_B / \text{PRF}_B \quad (1)$$

$$T_C = N_C \times \text{PS} / \text{PRF}_C \quad (2)$$

wherein $N_B$ represents the number of scan lines used to form the B-mode image, $\text{PRF}_B$ represents a pulse repetition frequency used to form the B-mode image, NC represents the number of the scan lines used to form the C-mode image, PS represents a packet size indicating repetition times of transmitting and receiving an ultrasound beam along one scan line, and $\text{PRF}_C$ represents a pulse repetition frequency used to form the C-mode image.

A ratio computing unit 112 may be operable to compute a time ratio of the first time $T_B$ to the second time $T_C$. The time ratio may be computed by dividing the first time $T_B$ by the second time $T_C$ in accordance with one embodiment of the present invention. For example, when the first time $T_B$ is 8 ms and the second time $T_C$ is 2 ms, the time ratio is 4(=8 ms/2 ms). When there is a fractional part in the division result, the time ratio may be determined with only integer part.

A determining unit 113 may be operable to compare the time ratio with a preset critical value (e.g., 1) to check whether the time ratio excesses the critical value. If the time ratio excesses the critical value, the determining unit 113 may output first determination information containing the time ratio. On the contrary, if not, the determining unit 113 may output second determination information.

Figure 3:
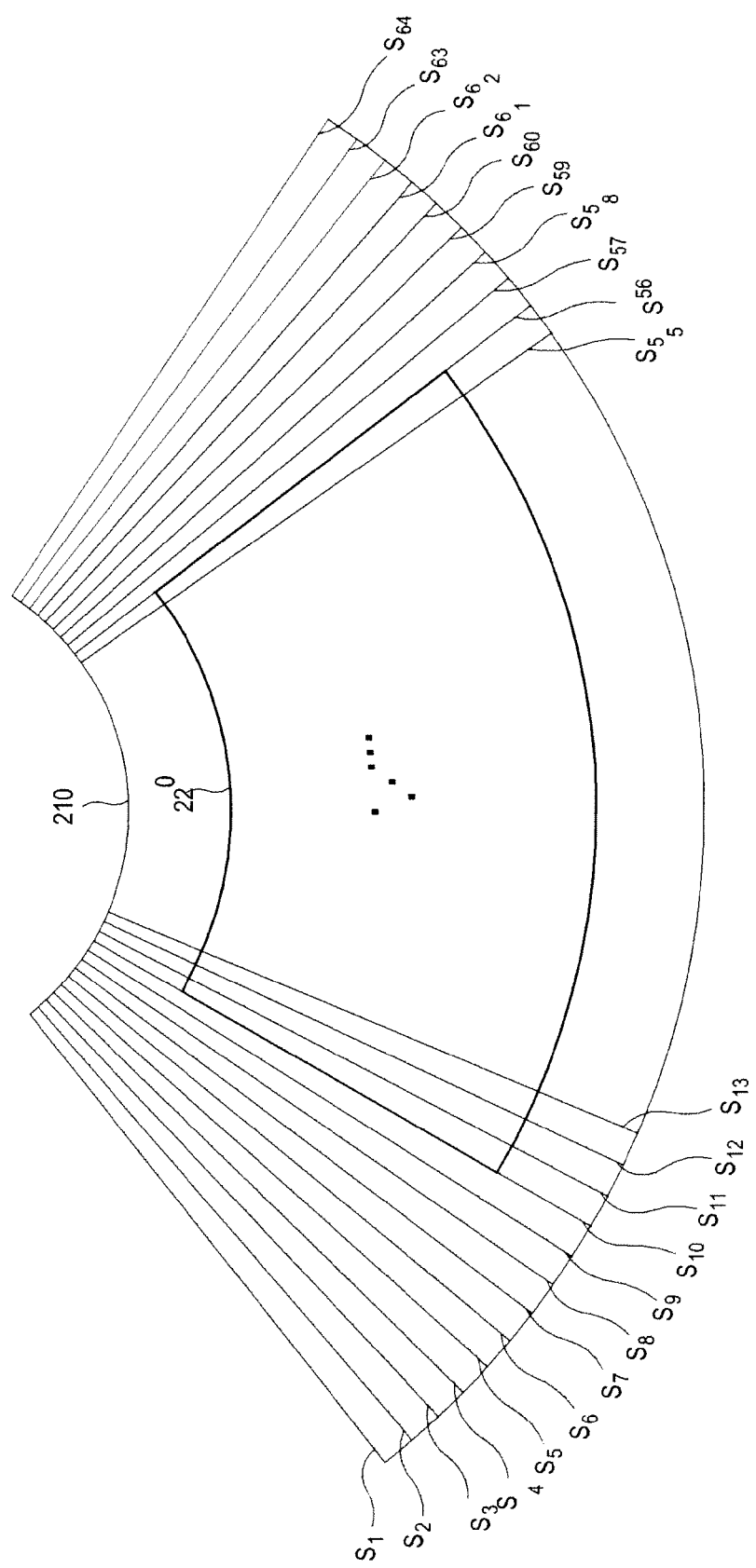
FIG. 3 is a schematic diagram illustrating a display example of a B-mode image, a plurality of scan lines and a color box.

If the first determination information is inputted, a scan line group setting unit 114 may be operable to set a plurality of scan line groups as many as the time ratio indicated by the first determination information. For example, when the time ratio is "4," scan lines $S_1$-$S_{64}$ illustrated in FIG. 3 may be divided into four scan line groups $SG_1$, $SG_2$, $SG_3$ and $SG_4$, as follows.

First scan line group SG1={$S_1$, $S_5$, $S_9$, $S_{13}$, $S_{17}$, ..., $S_{53}$, $S_{57}$, $S_{61}$}

Second scan line group SG2={$S_2$, $S_6$, $S_{10}$, $S_{14}$, $S_{18}$, ..., $S_{54}$, $S_{58}$, $S_{62}$}

Third scan line group SG3={$S_3$, $S_7$, $S_{11}$, $S_{15}$, $S_{19}$, ..., $S_{55}$, $S_{59}$, $S_{63}$}

Fourth scan line group SG4={$S_4$, $S_8$, $S_{12}$, $S_{16}$, $S_{20}$, ..., $S_{56}$, $S_{60}$, $S_{64}$}

A control signal generating unit 115 may be operable to generate a control signal for controlling transmission and reception of the ultrasound beam. The control signal may include a first control signal for controlling the formation of a B-mode image 210, i.e., a B-mode scan such that the ultrasound beam is transmitted are received along the scan lines $S_1$-$S_{64}$. The control signal may further include a second control signal for controlling the formation of the C-mode image, i.e., a C-mode scan such that the ultrasound beam is transmitted and received along scan lines $S_{10}$ to $S_{56}$ within a color box 220 set on the B-mode image 210 (see FIG. 3). The control signal also includes a third control signal for controlling the transmission and reception of the ultrasound beam such that the ultrasound beam for the B-mode image is alternately transmitted and received along scan lines included in the respective scan line groups.

If the second determination information is inputted from the determining unit 113, the control signal generating unit 115 may be operable to generate a fourth control signal for a B-mode scan such that the ultrasound beam is transmitted along scan lines $S_1$-$S_9$ and $S_{57}$-$S_{64}$, which do not belong to the color box 220.

The transmit/receive unit 120 may be operable to transmit the ultrasound beam along scan lines set in a target object and receive ultrasound echoes reflected from the target object in response to the control signal. If the first control signal is inputted from the control unit 110, the transmit/receive unit 120 may be operable to sequentially transmit the ultrasound beam along the scan lines $S_1$-$S_{64}$ in response to the first control signal and receive ultrasound echoes reflected from the target object to thereby form receive signals corresponding to the scan lines $S_1$-$S_{64}$ ("first receive signals") for a B-mode image. The first receive signals may include information associated with the scan lines, e.g., position information of the scan lines, position information of sampling points on the scan lines, data obtained at the sampling points and the like.

If the second control signal is inputted from the control unit 110, the transmit/receive unit 120 may be operable to transmit the ultrasound beam along the scan lines $S_{10}$-$S_{56}$ belonging to the color box 220 in response to the second control signal and receive ultrasound echoes reflected from the target object to thereby form receive signals corresponding to the scan lines $S_{10}$-$S_{56}$ ("second receive signals") for the C-mode image. The second receive signals may include information associated with the scan lines $S_{10}$-$S_{56}$, e.g., position information of the scan lines, position information of sampling points on the scan lines, data obtained from the sampling points and the like.

If the third control signal is inputted from the control unit 110, the transmit/receive unit 120 may be operable to transmit the ultrasound beam along the scan lines $S_1$, $S_5$, $S_9$, $S_{13}$, $S_{17}$, ..., $S_{53}$, $S_{57}$ and $S_{61}$ included in the first scan line group $SG_1$ and receive ultrasound echoes from the target object in response to the third control signal to thereby form receive signals corresponding to the scan lines included in the first scan line group $SG_1$ ("first scan line group receive signals"). The first scan line group receive signals may include information associated with the scan lines of the first scan line group $SG_1$, e.g., position information of the scan lines, position information of sampling points on the scan lines, data obtained from the sampling points and the like. Thereafter, if the second control signal is inputted, the transmit/receive unit 120 may be operable to transmit the ultrasound beam along the scan lines $S_{10}$-$S_{56}$ within the color box 220 and receive ultrasound echoes reflected from the target object in response to the second control signal to thereby form new second receive signals for a C-mode image.

Subsequently, if the third control signal is inputted from the control unit 110, the transmit/receive unit 120 may be operable to transmit the ultrasound beam along the scan lines $S_2$, $S_6$, $S_{10}$, $S_{14}$, $S_{18}$, ..., $S_{54}$, $S_{58}$ and $S_{62}$ included in the second scan line group $SG_2$ and receive ultrasound echoes from the target object in response to the third control signal to thereby form receive signals corresponding to the scan lines included in the second scan line group $SG_2$ ("second scan line group receive signals"). The second scan line group receive signals may include information associated with the scan lines of the first scan line group $SG_2$, e.g., position information of the scan lines, position information of sampling points on the scan lines, data obtained from the sampling points and the like. Thereafter, if the second control signal is inputted from the control unit 110, the transmit/receive unit 120 may be operable to transmit the ultrasound beam along the scan lines $S_{10}$-$S_{56}$ within the color box 220 and receive ultrasound echoes reflected from the target object in response to the second control signal to thereby form new second receive signals.

Successively, if the third control signal is inputted from the control unit 110, the transmit/receive unit 120 may be operable to transmit the ultrasound beam along the scan lines $S_3$, $S_7$, $S_{11}$, $S_{15}$, $S_{19}$, ..., $S_{55}$, $S_{59}$ and $S_{63}$ included in the third scan line group $SG_3$ and receive ultrasound echoes from the target object in response to the third control signal to thereby form receive signals corresponding to the scan lines included in the third scan line group $SG_3$ ("third scan line group receive signals"). The third scan line group receive signals may include information associated with the scan lines of the third scan line group $SG_3$, e.g., position information of the scan lines, position information of sampling points on the scan lines, data obtained from the sampling points and the like. Thereafter, the transmit/receive unit 120 may be operable to transmit the ultrasound beam along the scan lines $S_{10}$-$S_{56}$ within the color box 220 and receive ultrasound echoes reflected from the target object in response to the second control signal to thereby form new second receive signals.

If the third control signal is inputted again from the control unit 110, the transmit/receive unit 120 may be operable to transmit the ultrasound beam along the scan lines $S_4$, $S_8$, $S_{12}$, $S_{16}$, $S_{20}$, ..., $S_{56}$, $S_{60}$ and $S_{64}$ included in the fourth scan line group $SG_4$ and receive ultrasound echoes from the target object in response to the third control signal to thereby form receive signals corresponding to the scan lines included in the fourth scan line group $SG_4$ ("fourth scan line group receive signals"). The fourth scan line group receive signals may include information associated with the scan lines of the fourth scan line group $SG_4$, e.g., position information of the scan lines, position information of sampling points on the scan lines, data obtained from the sampling points and the like. Thereafter, the transmit/receive unit 120 may be operable to transmit the ultrasound beam along the scan lines $S_{10}$-$S_{56}$ within the color box 220 and receive ultrasound echoes reflected from the target object in response to the second control signal to thereby form new second receive signals. The transmit/receive unit 120 may be operable to repeat the above process until an end request is inputted.

In the meantime, if the fourth control signal is inputted from the control unit 110, the transmit/receive unit 120 may be operable to transmit the ultrasound beam along scan lines $S_1$-$S_9$ and $S_{57}$-$S_{64}$, which are not within the color box 220 among the scan lines S1-S64, and receive ultrasound echoes reflected from the target object to thereby form receive signals corresponding to the scan lines $S_1$-$S_9$ and $S_{57}$-$S_{64}$ ("third receive signals"). In such a case, the third receive signals may contain information associated with the scan lines $S_1$-$S_9$ and $S_{57}$-$S_{64}$, i.e., position information of the scan lines, position information of sampling points on the scan lines, data obtained at the sampling points and the like. Thereafter, if the second control signal is inputted from the control unit 110, the transmit/receive unit 120 may be may be operable to transmit the ultrasound beam along the scan lines $S_{10}$-$S_{56}$ within the color box 220 and receive ultrasound echoes reflected from the target object in response to the second control signal to thereby form new second receive signals. The transmit/receive unit 120 may be operable to repeat the above process until an end request is inputted from the control unit 110.

The storage unit 130 may sequentially store the first receive signals, the second receive signals, the first to fourth scan line group receive signals and the third receive signals.

Figure 4:
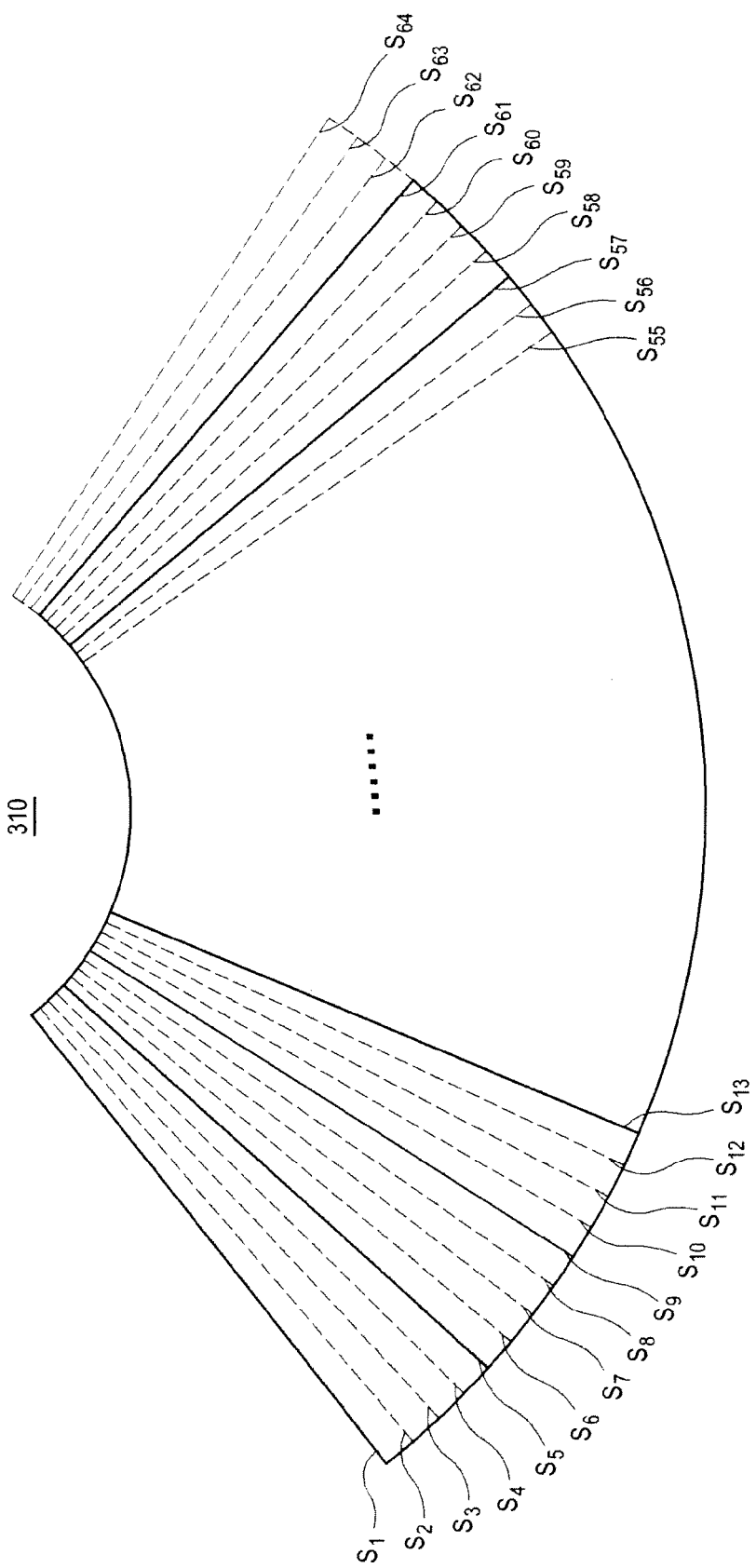
FIGS. 4 to 8 are schematic diagrams showing examples of forming a B-mode image in forming a BC-mode image in accordance with one embodiment of the present invention.

The image processing unit 140 may be operable to extract the first receive signals from the storage unit 130 and form a B-mode image based on the first receive signals. The image processing unit may operable to extract the second receive signals from the storage unit 130 and form a C-mode image based on the extracted second receive signals. The image processing unit 140 may be operable to combine the B-mode image with the C-mode image to form a BC-mode image. Subsequently, the image processing unit 140 may be operable to extract the first scan line group receive signals and first receive signals in which first receive signals corresponding to the scan lines $S_1$, $S_5$, $S_9$, $S_{13}$, $S_{17}$, . . . , $S_{53}$, $S_{57}$ and $S_{61}$ included in the first scan line group $SG_1$ are excluded, and then update the first receive signals with the extracted first scan line group receive signals. The image processing unit 140 may be operable to form a B-mode image 310 based on the updated first receive signals, as illustrated in FIG. 4. The image processing unit may extract the new second receive signals from the storage unit 130 and form a C-mode image based on the extracted second receive signals. Thereafter, the image processing unit 140 may be operable to combine the B-mode image 310 with the C-mode image to form a BC-mode image.

Figure 5:
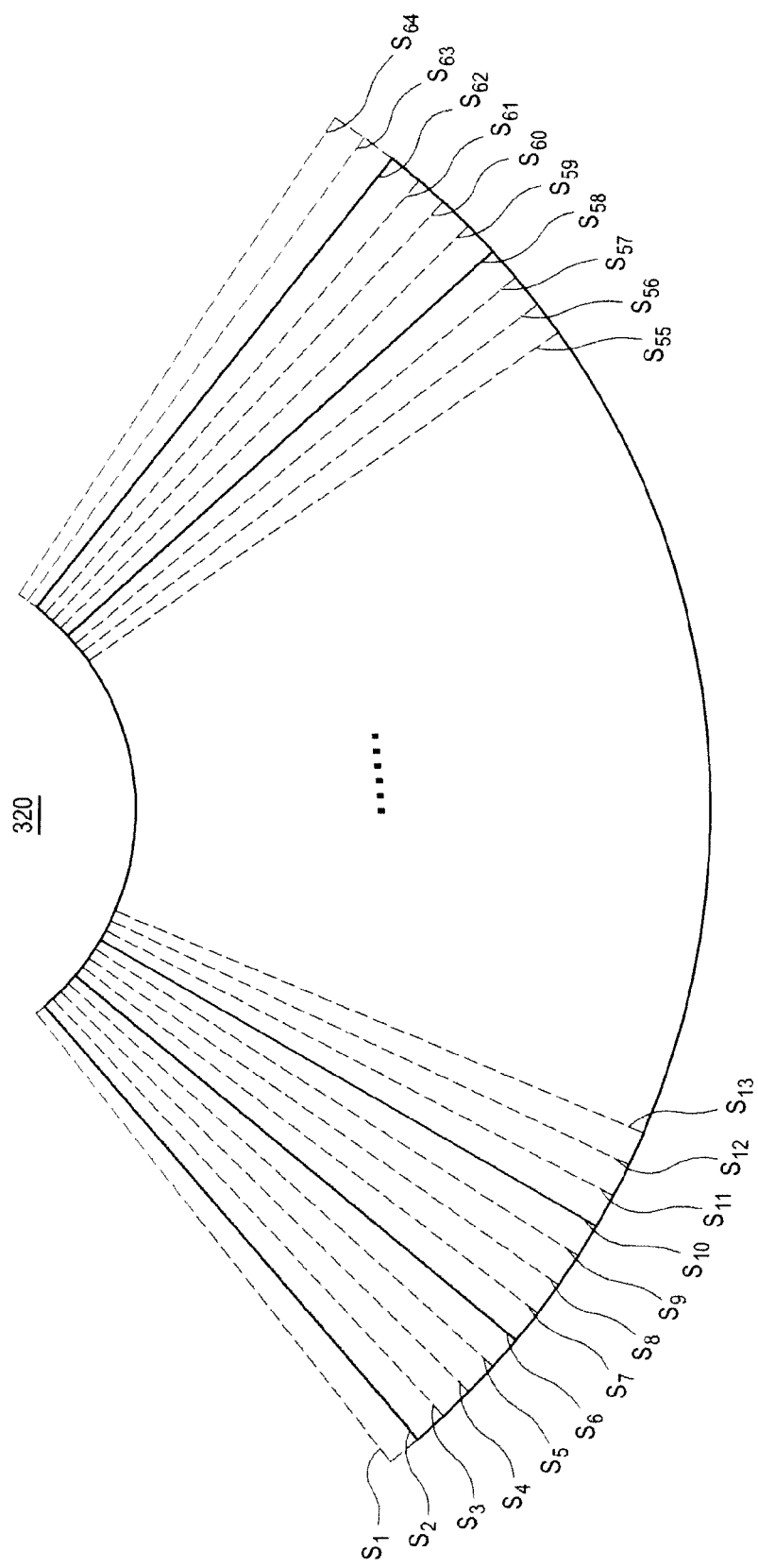

The image processing unit 140 may be operable to extract the second scan line group receive signals and first receive signals excepting the receive signals corresponding to the scan lines included in the second scan line group $SG_2$ to update the first receive signals. The image processing unit 140 may be operable to form a B-mode image 320 based on the updated first receive signals, as illustrated in FIG. 5. The image processing unit may extract the new second receive signals from the storage unit 130 and form a C-mode image based on the extracted new second receive signals. Thereafter, the image processing unit 140 may be operable to combine the B-mode image 320 with the C-mode image to form a BC-mode image.

Figure 6:
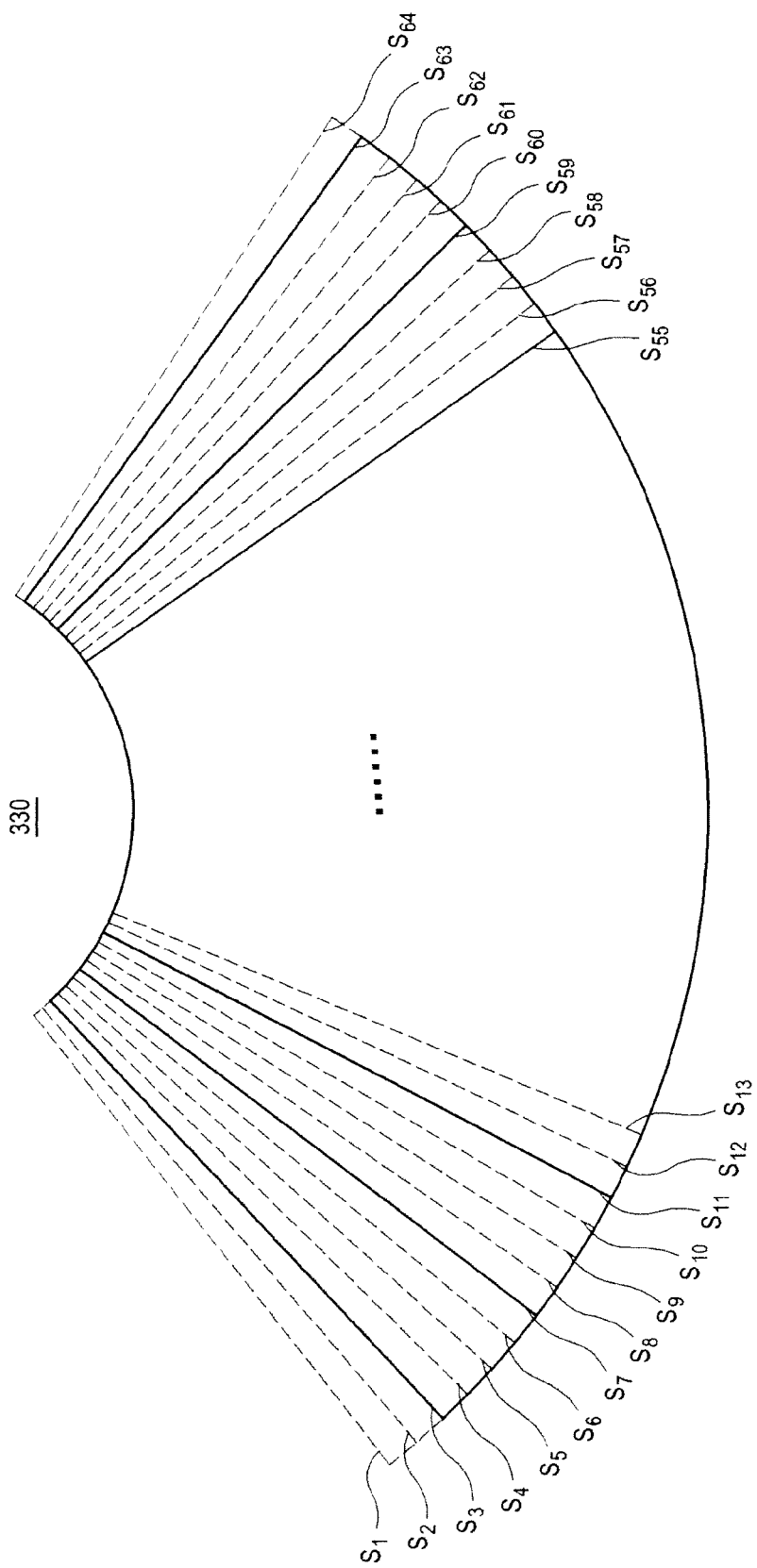

The image processing unit 140 may be operable to extract the third scan line group receive signals and first receive signals in which the receive signals corresponding to the scan lines included in the third scan line group $SG_3$ are excluded to update the first receive signals. The image processing unit 140 may be operable to form a B-mode image 330 based on the updated first receive signals, as illustrated in FIG. 6. The image processing unit may extract the new second receive signals from the storage unit 130 and form a C-mode image based on the extracted second receive signals. Thereafter, the image processing unit 140 may be operable to combine the B-mode image 330 with the C-mode image to form a BC-mode image.

Figure 7:
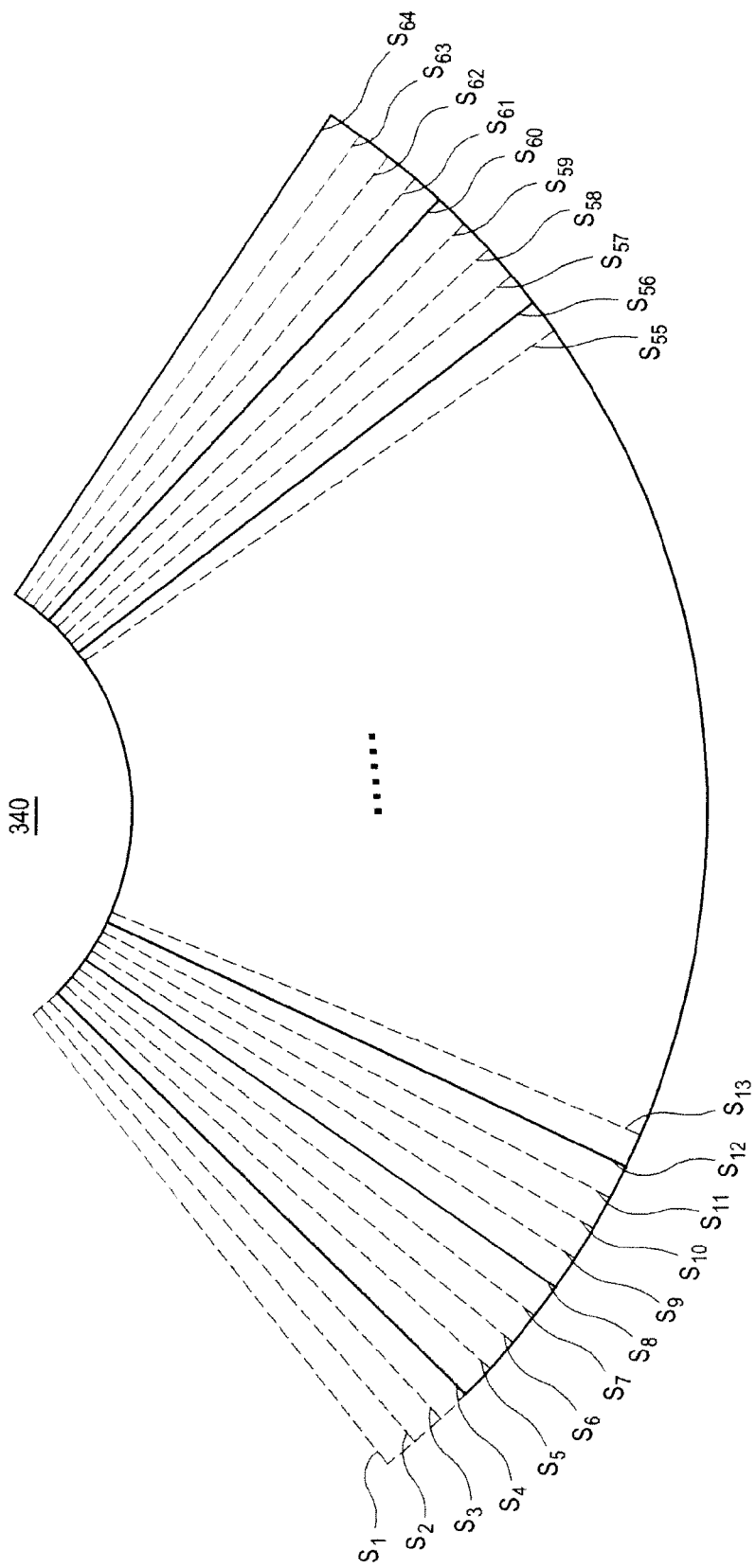

The image processing unit 140 may be operable to extract the fourth scan line group receive signals and first receive signals in which the receive signals corresponding to the scan lines included in the fourth scan line group $SG_4$ are excluded to update the first receive signals. The image processing unit 140 may be operable to form a B-mode image 340 based on the updated first receive signals, as illustrated in FIG. 7. The image processing unit may extract the new second receive signals from the storage unit 130 and form a C-mode image based on the extracted second receive signals. Thereafter, the image processing unit 140 may be operable to combine the B-mode image 340 with the C-mode image to form a BC-mode image. The image processing unit 140 may repeatedly carry out the above process until an end request is inputted from the control unit 110.

Figure 8:
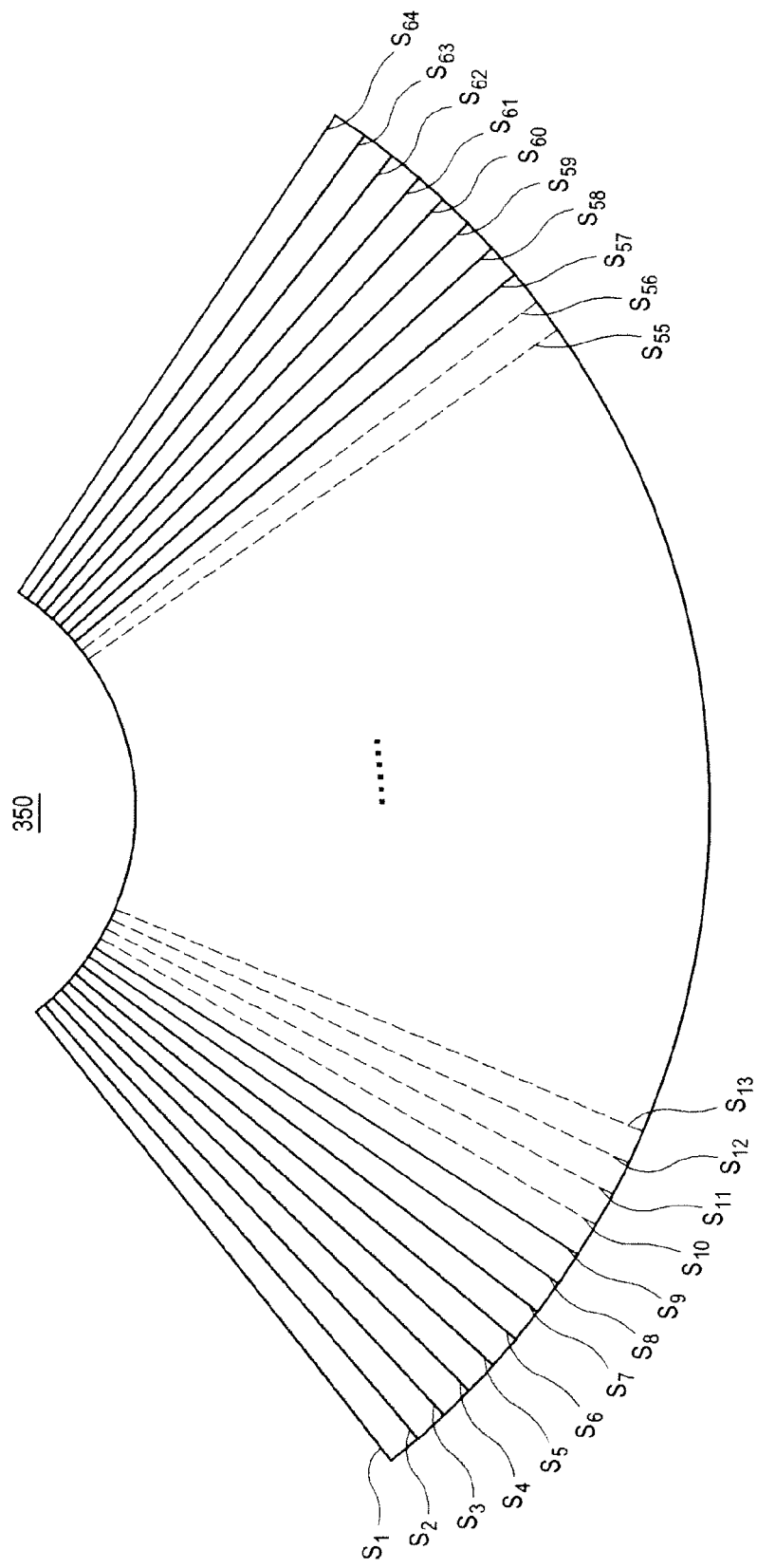

In the meantime, the image processing unit 140 may extract the third receive signals and the first receive signals from the storage unit 130, and then from a B-mode image 350 based on the extracted third and second receive signals, as illustrated in FIG. 8. Thereafter, the image processing unit 140 may extract the second receive signals and form a C-mode image based on the extracted second receive signals. The image processing unit 140 may combine the B-mode image with the C-mode image to form a BC-mode image.

The display unit 150 may be operable to display the B-mode image and the BC-mode image formed in the image processing unit 140.

As mentioned above, since the time required to form the B-mode image may be reduce in accordance with the present invention, the frame rate of the BC-mode image may be improved. Thus, an ultrasound image of a rapidly moving target object may be clearly provided.

In accordance with one embodiment of the present invention, there is provided an ultrasound system, comprising: a control unit operable to generate a first control signal for a B-mode scan and a second control signal for a C-mode scan; an input unit operable to receive color box information for setting a color box; a transmit/receive unit responsive to the first and second control signals and operable to transmit ultrasound signals along a plurality of scan lines set in a target object and form receive signals based on the ultrasound echo signals reflected from the target object, said receive signals including first receive signals corresponding to the scan lines formed in response to the first control signal and second receive signals corresponding to a portion of scan lines within the color box formed in response to the second control signal; an image processing unit operable to form a B-mode image and a C-mode image based on the first and second receive signals, and combine the B-mode image with the C-mode image to form a BC-mode image, wherein the control unit is further operable to compute a time ratio of a first time required to form the B-mode image to a second time required to form the C-mode image, and generate a third control signal for a B-mode scan along scan lines, which are not within the color box, based on the time ratio, wherein the receive signals further include third receive signals formed in response to the third control signal, and the image processing unit is further operable to form a B-mode image based on the third receive signals and the second signals.

In accordance with another embodiment of the present invention, there is provided a method of forming a BC-mode image, comprising: a) generating a first control signal for a B-mode scan and a second control signal for a C-mode scan; b) transmitting ultrasound signals along a plurality of scan lines set in a target object and form first receive signals based on the ultrasound echo signals reflected from the target object in response to the first control signals; c) forming a B-mode image based on the first receive signals; d) receiving color setup information for setting a color box on the B-mode image; e) transmitting ultrasound signals along scan lines within the color box in response to the second control signal; f) combining the B-mode image with the C-mode image to form a BC-mode image; g) computing a time ratio of a first time required to form the B-mode image to a second time required to form the C-mode image; h) generating a third control signal for a B-mode scan along scan lines, which are not within the color box, based on the time ratio, to form third receive signals; i) forming a new B-mode image based on the third receive signals and the second signals; j) generating the second control signal to thereby form new C-mode image and combining the new B-mode image with the new C-mode image to form a new BC-mode image; and i) repeating h) to j).

Any reference in this specification to "one embodiment," "an embodiment," "example embodiment," etc. means that a particular feature, structure or characteristic described in connection with the embodiment is included in at least one embodiment of the present invention. The appearances of such phrases in various places in the specification are not necessarily all referring to the same embodiment. Further, when a particular feature, structure or characteristic is described in connection with any embodiment, it is submitted that it is within the purview of one skilled in the art to effect such feature, structure or characteristic in connection with other ones of the embodiments.

Although embodiments have been described with reference to a number of illustrative embodiments thereof, it should be understood that numerous other modifications and embodiments can be devised by those skilled in the art that will fall within the spirit and scope of the principles of this disclosure. More particularly, numerous variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

What is claimed is:

1. An ultrasound system, comprising:
    a transmitter/receiver configured to transmit ultrasound signals along a plurality of scan lines set in a target object and to receive ultrasound echo signals from the target object to output receive signals;
    a controller configured to control the transmitter/receiver to perform a B-mode scan along all of the plurality of scan lines to obtain first receive signals;
    an image processor configured to form a B-mode image based on the first receive signals;
    a display unit configured to display the B mode image formed in the image processor; and
    an input device configured to receive color box information for setting a color box, which is defined as a portion of a scan region scanned by the plurality of scan lines and is set based on a user input, for obtaining a C-mode image corresponding to a region set as the color box on the B-mode image,
    wherein:
    the controller is further configured to determine a first group of scan lines included in the color box and a second group of scan lines not included in the color box based on the color box information and to control the transmitter/receiver to perform a C-mode scan along the first group of scan lines to obtain second receive signals,
    the image processor is configured to form a C-mode image based on the second receive signals and to combine the B-mode image and the C-mode image to form a BC-mode image, and
    the controller is further configured to control the transmitter/receiver to perform a B-mode scan along the second group of scan lines to obtain third receive signals,
    the image processor is further configured to form a new B-mode image by updating the first receive signals with the third receive signals and the second receive signals, and
    wherein the input device and the image processor are implemented as hardware devices.

2. The ultrasound system of claim 1, wherein, after the image processor forms the new B-mode image, the controller is further configured to control the transmitter/receiver to perform a C-mode scan along the first group of scan lines to obtain new second receive signals, and the image processor is configured to form a new C-mode image based on the new second receive signals and to combine the new B-mode image with the new C-mode image to form a new BC-mode image.

3. The ultrasound system of claim 2, further comprising a memory to store the first, second and third receive signals.

4. A method of forming a BC-mode image in an ultrasound system, the method comprising:
    transmitting, using a transmitter/receiver, ultrasound signals along a plurality of scan lines set in a target object and receiving ultrasound echo signals from the target object to output receive signals;
    performing, using a controller, a B-mode scan along all of the plurality of scan lines to obtain first receive signals;
    forming a B-mode image, using an image processor, based on the first receive signals;
    receiving, at an input device, color box information for setting a color box, which is defined as a portion of a scan region scanned by the plurality of scan lines and is set based on a user input, on the B-mode image;
    determining, using the image processor, a first group of scan lines included in the color box and a second group of scan lines not included in the color box based on the color box information;
    performing, using the controller, a C-mode scan along the first group of scan lines to obtain second receive signals;
    forming, using the image processor, a C-mode image based on the second receive signals;
    combining, using the image processor, the B-mode image and the C-mode image to form a BC-mode image;
    performing, using the controller, a B-mode scan along the second group of scan lines to obtain third receive signals;
    forming a new B-mode image, using the image processor, by updating the first receive signals with the third receive signals and the second receive signals; and
    displaying, using a display unit, the new B-mode image,
    wherein the input device and the image processor are implemented as a hardware devices.

5. The method of claim 4, further comprising:
    performing, using the controller, a C-mode scan along the first group of scan lines to obtain new second receive signals;
    forming, using the image processor, new C-mode image based on the new second receive signals; and combining, using the image processor, the new B-mode image with the new C-mode image to form a new BC-mode image.

6. The method of claim 5, further comprising storing, at a memory, the first, second and third receive signals.

* * * * *